United States Patent [19]
Don Michael

[11] Patent Number: 5,176,638
[45] Date of Patent: Jan. 5, 1993

[54] REGIONAL PERFUSION CATHETER WITH IMPROVED DRUG DELIVERY CONTROL

[76] Inventor: T. Anthony Don Michael, 309 Panorama Dr., Bakersfield, Calif. 93305

[21] Appl. No.: 704,083

[22] Filed: May 22, 1991

Related U.S. Application Data

[63] Continuation-in-part of Ser. No. 526,260, May 21, 1990, and a continuation-in-part of Ser. No. 492,582, Mar. 13, 1990, and a continuation-in-part of Ser. No. 464,029, Jan. 12, 1990, abandoned.

[51] Int. Cl.$^5$ .................................. A61M 29/00
[52] U.S. Cl. ........................ 604/101; 606/192; 606/194; 604/265; 128/207.15
[58] Field of Search ............... 604/96–103, 604/890.1, 264, 265; 606/191, 192, 194; 623/1, 12; 128/207.15

[56] References Cited

U.S. PATENT DOCUMENTS

| | | | |
|---|---|---|---|
| 5,049,1321 | 9/1991 | Shaffer et al | 604/96 |
| 3,799,173 | 3/1974 | Kamen | 128/207.15 |
| 3,882,852 | 5/1975 | Sinnreich | 604/96 |
| 4,423,725 | 1/1984 | Bovan et al. | 604/101 |
| 4,573,966 | 3/1986 | Weikl et al. | 604/101 |
| 4,636,195 | 1/1987 | Wolinsky | 604/101 |
| 4,784,647 | 11/1988 | Gross | 604/265 |
| 4,798,585 | 1/1989 | Inoue et al. | 604/891.1 |
| 4,994,033 | 2/1991 | Shockey et al. | 604/96 |
| 5,046,503 | 9/1991 | Scheideman | 604/96 |
| 5,049,140 | 9/1991 | Brenner et al. | 604/265 |
| 5,059,178 | 10/1991 | Ya | 604/96 |

*Primary Examiner*—C. Fred Rosenbaum
*Assistant Examiner*—Chalin Smith
*Attorney, Agent, or Firm*—Spensley Horn Jubas & Lubitz

[57] ABSTRACT

A medical or biological treatment device for creating a controlled "minienvironment" and which supplies a treatment or diagnostic modality to a region of a physiologic passage, the device including: a catheter having an outer surface, a distal end and a proximal end and having a blood bypass flow passage extending from the outer surface of the catheter at a first location between the proximal and distal ends and along the interior of the catheter to a location spaced distally from the first location; an inflatable balloon extending around the catheter and secured at the outer surface of the catheter; and a perforated fluid transfer member carried by the catheter and secured at the outer surface of the catheter between the balloon and the first location for permitting transfer of fluid to and from a region surrounding the fluid transfer member. The delivery system is designed to deliver one or more agents whose concentration can be varied to obtain an optimal effect in a "minienvironment" and to maintain nontoxic concentrations at other sites in the body.

14 Claims, 2 Drawing Sheets

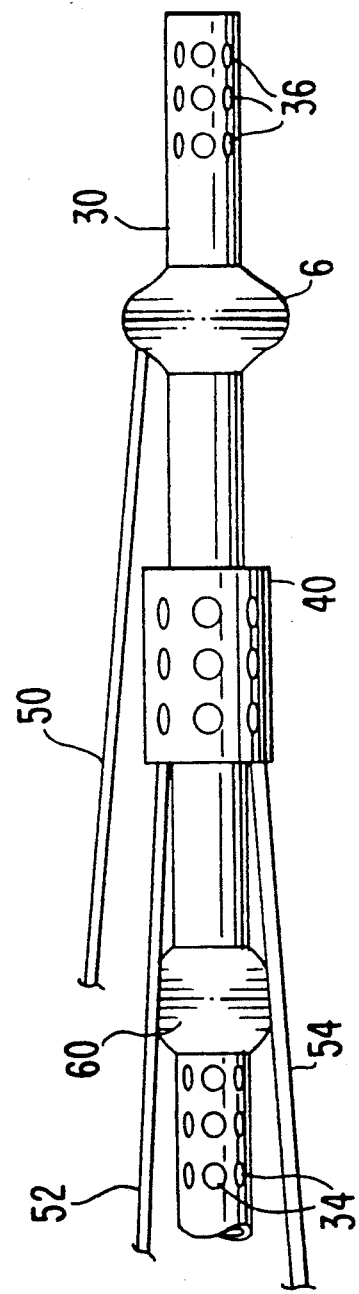
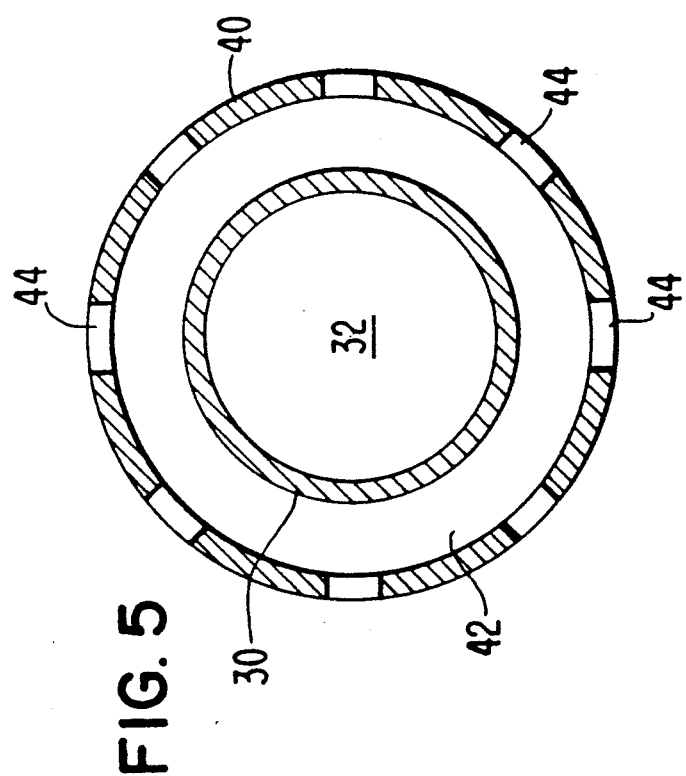

REGIONAL PERFUSION CATHETER WITH IMPROVED DRUG DELIVERY CONTROL

CROSS REFERENCE TO RELATED APPLICATIONS

This application is a continuation-in-part of application Ser. Nos. 07/464,029, filed Jan. 12, 1990 abandoned; 07/492,582, filed Mar. 13, 1990; and 07/526,260, filed May 21, 1990, the disclosures of which are incorporated herein by reference.

BACKGROUND OF THE INVENTION

The present invention relates to medical treatments which require delivery of a chemical or biological material to a defined region in a physiologic passage, which may be a blood vessel, the urinary canal, or some other passage.

For example, it may be desired to remove blockages and deposits associated with medical conditions of a wide degree of severity, ranging from those which produce physical discomfort to those which are life threatening. In addition, there are known chemical and biological materials which are effective to prevent restenosis or cell division, or which may be used, for various medical purposes, to coat the wall of a physiologic passage.

Accordingly, a large number of techniques offering the possibility of performing such procedures have been investigated. Among these techniques are those involving the use of appropriate dissolution chemicals. However, while such chemicals and biological materials are known, these materials also produce side effects in the human body which have prevented their safe use.

The preceding applications, cited above, disclose the details of a procedure which allows a dissolution chemical to be partially localized and concentrated at the site of a deposit and allows the relative proportions of dissolution chemical and blood to be adjusted. The concept of this approach is to create a controlled minienvironment.

It has now been found that the apparatus previously employed for carrying out this method did not allow complete control of the conditions essential to optimum implementation of the method i.e., the calibration and control of the "minienvironment" so designated as the area under treatment in a manner which enables optimal effects to be obtained within this environment while minimizing the toxic effects of the chemical or biological material to other sites in the body.

SUMMARY OF THE INVENTION

It is an object of the present invention to provide improved apparatus which will permit better control of such treatment processes.

Another object of the invention is to provide apparatus which will particularly facilitate delivery of chemical or biological materials to the treatment site at a controlled rate, while permitting periodic sampling operations to be performed.

Yet another object of the invention is to facilitate maintenance of the desired chemical/blood ratio at the treatment site.

An additional object of the invention is to allow localized and controlled delivery of a chemical or biological material initially provided in solid form to a region of a physiological passage.

The above and other objects are achieved, according to the present invention, by a medical treatment device for supplying a treatment chemical to a region of a physiologic passage, the device comprising:

a catheter having an outer surface, a distal end and a proximal end and having a bypass flow passage extending from the outer surface of the catheter at a first location between the proximal and distal ends and along the interior of the catheter to an outlet opening at a second location spaced distally from the first location;

an inflatable balloon extending around the catheter and secured at the outer surface of the catheter at a third location between the first and second locations;

a perforated fluid transfer member carried by the catheter and secured at the outer surface of the catheter at a fourth location between the first and third locations, the fluid transfer member being configured to define an annular chamber with the outer surface of the catheter;

first conduit means communicating with the balloon for supplying an inflation fluid thereto; and second conduit means communicating with the annular chamber for conducting fluid to and from the annular chamber.

Preferably, the device further includes a body of porous material surrounding the catheter and secured at the outer surface of the catheter in a region between the first and second locations for restricting fluid flow in the passage.

In further accordance with the invention, the catheter may carry a body, comparable to a stent, containing a second chemical or biological material in a form to be released at a controlled rate. Because the device according to the invention creates a closed region in a physiologic passage, such a body can be fabricated to release the material at a higher rate than is normally established for conventional stents.

Essentially, a device according to the invention permits a controlled environment to be created in a selected region of a physiologic passage, whereby a high concentration of a treatment agent, coating material, or other substance can be established while protecting the remainder of the patient's body from high concentration of such materials.

BRIEF DESCRIPTION OF THE DRAWING

FIG. 4 is a view similar to that of FIG. 1 showing a second embodiment of a treatment device according to the invention.

FIG. 5 is a cross-sectional view taken along a plane perpendicular to the axis of the device shown in FIG. 4.

DESCRIPTION OF THE PREFERRED EMBODIMENTS

While, as noted above, a device according to the invention has a wide range of uses, embodiments intended for introduction into blood vessels will be described below, solely by way of example.

Figure 1:
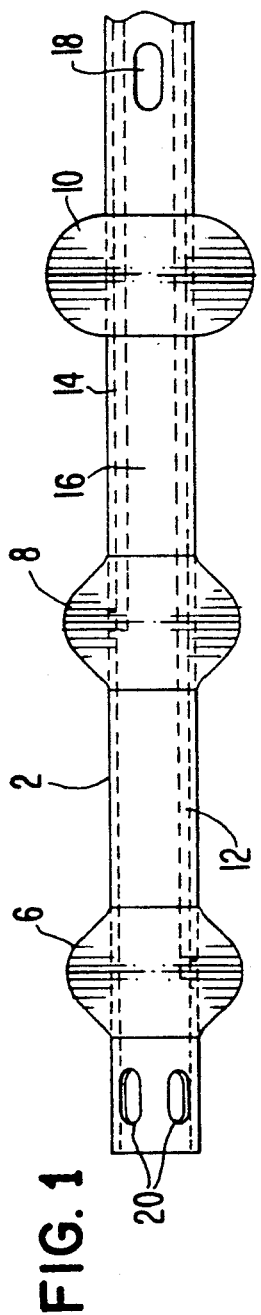
FIG. 1 is a side elevational view illustrating one embodiment of a treatment device according to the invention.

FIG. 1 illustrates an exemplary embodiment of a treatment device according to the invention composed of a catheter 2 carrying an inflatable balloon, or cuff, 6, a fluid transfer member 8 and, optionally but desirably, a porous fluid flow restricting member 10.

Catheter 2 is formed to have a balloon inflation lumen 12, a fluid conveying lumen 14 and a blood bypass flow lumen 16. Preferably, these are the only lumens provided in catheter 2, which allows the catheter to be given a small diameter.

Lumen 12 extends from the proximal end (not shown) of catheter 2 to the region of balloon 6, and lumen 12 then extends radially through the outer peripheral surface of catheter 2 to communicate with the region enclosed by balloon 6 in order to supply an inflation fluid, e.g. $CO_2$, thereto. Preferably, balloon 6 is a high compliance, low pressure balloon which, when inflated, can either partially or substantially completely obturate the blood vessel in which the device has been inserted while applying only a minimal pressure to the blood vessel wall. The inflation of balloon 6 can be controlled to leave a small gap for fluid flow between itself and the blood vessel wall, which may prove desirable in certain situations.

Lumen 14 extends from the proximal end of catheter 2 to the region of fluid transfer member 8 and then extends radially through the outer peripheral surface of catheter 2 to communicate with the region enclosed by member 8.

Lumen 14 is connected at the proximal end of catheter 2 to a unit which can deliver dissolution chemical at a controlled rate to the region enclosed by member 8 and can withdraw fluid for sampling purposes from the region enclosed by member 8. Member 8 is provided with perforations which permit a controlled flow of fluid between the region enclosed by member 8 and the region surrounding that member.

Member 10, if provided, is of a soft, porous material, e.g. surgical sponge material, and is dimensioned to carry biodegradable material and to obturate at least a substantial portion of the flow path through the blood vessel.

The essential purpose of member 10 is to limit the rate of flow of fluid therepast while eliminating certain complexities associated with a further inflatable balloon, including the need for a further inflation lumen and apparatus for controlling the delivery of inflation fluid to that balloon. Member 10 may additionally serve as a drug delivery vehicle, as will be discussed below.

Prior to insertion of catheter 2 into a blood vessel, member 10 may be compressed against the outer surface of catheter 2 by a conventional caging device in order to facilitate catheter insertion. When catheter 2 is in position, the caging device is actuated, e.g. via a wire extending to the proximal end of catheter 2, to permit member 10 to expand into the condition shown in FIG. 1.

Thus, the region bounded longitudinally by balloon 6 (when inflated) and member 10, and radially by catheter 2 and the blood vessel wall form a treatment chamber in which a desired fluid composition can be maintained. To this end, any fluid flow into or out of this chamber, past balloon 6 or member 10, is limited by the fact that any gap between balloon 6 or member 10 and the blood vessel wall has a small area and member 10 is of a material which permits only a limited rate of flow therethrough.

Lumen 16 is provided to allow a sufficient flow of blood past the treatment chamber to body regions downstream thereof. For this purpose, lumen 16 is given a sufficiently large diameter, larger than those of lumens 12 and 14, and communicates with regions surrounding catheter 2 via one or more inlet openings 18 and one or more outlet openings 20. Openings 18 are spaced proximally of member 10 and openings 20 are spaced distally of balloon 6. In addition, lumen 16 preferably extends fully to the distal end of catheter 2 so that blood flowing through lumen 16 can exit directly via the distal end of catheter 2.

Figure 2:
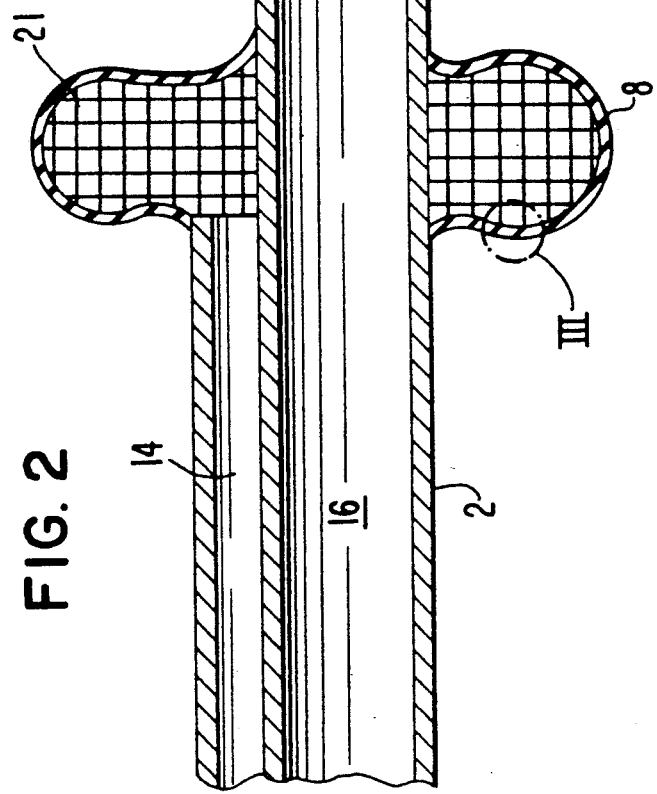
FIG. 2 is a cross-sectional detail view of a portion of the device of FIG. 1.

FIG. 2 shows in greater detail member 8 of the device of FIG. 1 which serves to deliver dissolution chemical to the treatment site, and which also allows for the withdrawal of fluid samples from the site.

Figure 3:
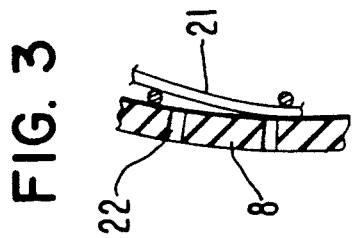
FIG. 3 is a cross-sectional detail view of the region enclosed in the circle III of FIG. 2.

Member 8 is composed of an elastically expandable rubber balloon or cuff which may be supported by a mesh armature of a relatively stiff material or framework 21. Framework 21 is sufficiently stiff to maintain the balloon or cuff in what appears from the outside to be a partially inflated condition. As can best be seen in the detail view of FIG. 3, the balloon or cuff is provided with a pattern of holes 22 and is held by framework 21 in a condition such that holes 22 have an effective diameter sufficient to permit the passage of a suitable quantity of fluid delivered to the region enclosed by member 8 via supply lumen 14.

The rate of delivery of a fluid from the region enclosed by the balloon or cuff of member 8 to the treatment region will depend on the pressure with which the fluid is delivered to the region enclosed by the balloon or cuff and the total effective flow diameter provided by all of holes 22. Preferably, the number and diameter of holes 22 is selected so that the range over which the supply pressure of the fluid can vary will correspond to the range over which it is desired to adjust the fluid flow rate.

If the fluid flow rate must be increased rapidly, for example in order to respond to an emergency condition, or because it is apparent that the desired treatment must be completed quickly, an increase in the delivery pressure above a certain level will result in at least some expansion of the balloon or cuff of member 8 and this, in turn, will act to increase the diameters of holes 22. Under these circumstances, the rate of change of fluid flow out of the balloon or cuff of member 8 will be an increasing function of an increase of the supply pressure.

A dissolution treatment of the type contemplated by the present invention is most effective, i.e., effects dissolution at the highest rate, if the treatment chemical employed, which may be any known clot-dissolving and preventing or thrombolytic agent such as that marketed under the tradename Hirudin, is present at the treatment site in mixture with certain blood components, e.g. enzymes. Moreover, the effectiveness of the dissolution agent will be dependent on the relative proportions of the agent and the blood components which cooperate with the agent. It is therefore desirable to periodically monitor the composition of the fluid at the treatment site and, according to the invention, this may be achieved by extracting samples of that fluid via holes 22 and lumen 14. Although the sampling operation is associated with a lower pressure in the region enclosed by member 8 than in the treatment region, the effect of framework 21 is to maintain holes 22 open, so that the desired sample can be withdrawn.

After a sample has been withdrawn and analyzed, the desired proportions of dissolution agent and blood in the treatment region can be adjusted by varying the rate at which the dissolution agent is subsequently delivered to the treatment region via lumen 14 and/or partially deflating balloon 6.

Because samples can be taken from the treatment site via openings 22 and lumen 14, an additional lumen, or a second catheter, need not be provided for sampling purposes.

Member 10, since it allows a restricted fluid flow, permits replenishment of the blood content in the treatment region while limiting the quantity of dissolution agent which is permitted to leave the treatment region.

A second embodiment of a treatment device according to the invention is illustrated in FIGS. 4 and 5. This device includes a catheter 30 composed of a hollow cylindrical member whose entire interior 32 constitutes a blood bypass flow lumen which communicates with the region exterior to catheter 30 via upstream openings 34 in the wall of catheter 30 and downstream openings 36 in the wall of catheter 30. In addition, lumen 32 extends fully to the distal end of catheter 30 and thus itself opens directly into the interior of the blood vessel. In this embodiment, openings 34 and 36 constitute the only openings in the wall of catheter 30.

Between openings 34 and 36 there is disposed cylinder 40 which surrounds catheter 30. The axial ends of cylinder 40 are connected to the outer surface of catheter 30 so that there is formed between the outer surface of catheter 30 and the inner surface of cylinder 40 a chamber 42 which is closed at its axial ends.

Cylinder 40 is constructed to be substantially rigid, although it may have a limited degree of flexibility.

The wall of cylinder 40 is provided with an array of openings 44 distributed around the circumference and along the length of cylinder 40 to provide fluid flow passages between chamber 42 and the region surrounding cylinder 40.

Balloon 6 is mounted on the outer surface of catheter 30 between cylinder 40 and outlet openings 36.

In this embodiment, a plurality of small diameter tubes is provided to conduct inflation gas to and from balloon 6, dissolution agent to chamber 42 and fluid samples from chamber 42. These tubes include a first tube 50 connected to balloon 6 and communicating with the region enclosed by balloon 6, a dissolution agent supply tube 52 and a sample withdrawal tube 54. Tubes 52 and 54 extend through one end wall of cylinder 40 to communicate with chamber 42. Exterior to the patient's body, tube 50 is connected to a source of inflating fluid, typically $CO_2$, tube 52 is connected to a pump for delivering the selected dissolution agent, and tube 54 is connected to a sample withdrawal pump.

By the provision of two separate tubes 52 and 54, switching between dissolution agent delivery phases and sample withdrawal phases can be accomplished more quickly.

Tubes 50, 52 and 54 may be secured, in any suitable manner, to catheter 30 at one or more locations along the length thereof. Alternately, tubes 50, 52 and 54, which may be of any suitable metal or plastic, may be held against catheter 30 in the region exterior to the patient's body, in which case they will remain adjacent catheter 30 between the point where they are held and their distal ends.

Since catheter 30 of the embodiment shown in FIGS. 4 and 5 contains only a single lumen and is provided only with lateral openings 34 and 36, it can be fabricated in a very simple manner and can be given a relatively small diameter.

The precise manner in which a device according to the present invention may be utilized to perform a dissolution operation is described in detail in the above-cited applications, and will not be repeated herein.

In further accordance with the invention, catheter 2 or 30 may include a carrier element containing a chemical or biological material in a form which allows release into the surrounding fluid at a controlled rate. Such a carrier element can be fabricated according to known techniques utilized for implantable stents. Since, the device according to the invention creates a closed or semi-closed environment at the treatment site, the material can be arranged to be released at a higher rate than is permitted in conventional stents. The material provided in this manner can be in addition to the chemical or biological agent delivered via member 8 or 40 to produce a combined or cooperative effect at the treatment site.

According to one possibility, the additional material, which can release drug or biological material and may be biodegradable, can be incorporated into porous member 10 of FIG. 1. Alternatively, the element containing the additional material could be in the form of separate rings 60 slipped around catheter 30 as shown in FIG. 4. Ring 60 may also be of a sponge material or biodegradable material as previously described.

The additional material may be incorporated into a carrier which is applied as a coating to, or impregnated in, member 10 or 60. The carrier may be a hydrophilic material or sponge which expands by absorbing surrounding liquid to release the material. Such expansion may additionally partially obstruct the passage in which the catheter is disposed.

In the case of the embodiment of FIG. 4, ring 60 may be disposed at any point between bypass holes 34 and balloon 6; in FIG. 1, if a separate element is provided it can be located anywhere between balloon 6 and member 10.

One advantage of providing such an element on catheter 2 or 30 is that the catheter can remain in place for any desired period of time so that a separate surgical procedure is not required to remove the element as in the case of conventional stents.

In the case of the embodiment shown in FIGS. 4 and 5, the fluid composition in the treatment region can be controlled by any combination of: The degree of obturation produced by balloon 6; the rate of delivery of material to chamber 42; the longitudinal location of holes 34; and the location of a body containing a treatment material along the length of catheter 30.

In further accordance with the invention, a ring such as 60 can be mounted near the distal end of catheter 2 or 30 and may be of a material of the type described above which expands by absorbing liquid to not only press gently against the walls of the passage but also to be loosened relative to the catheter. As a result, the catheter can be withdrawn from the passage while leaving the ring in place while a chemical or biological agent contained in the ring continues to be released at a controlled rate. In this case, the ring should be made entirely of biodegradable material so that it will dissolve completely within a suitable period of time.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A medical or biological treatment device for supplying a treatment chemical to a region of a physiologic passage, said device comprising:
    a catheter having an outer surface, a distal end and a proximal end and having a bypass flow passage extending from the outer surface of said catheter at a first location between said proximal and distal ends and along the interior of said catheter to an outlet opening at a second location spaced distally from said first location to allow unimpeded low pressure blood or fluid flow to organs downstream of said catheter;
    an inflatable balloon extending around said catheter and secured at said outer surface of said catheter at a third location between said first and second locations;
    a perforated fluid transfer member carried by said catheter and secured at said outer surface of said catheter at a fourth location between said first and third locations, said fluid transfer member being configured to define an annular chamber with said outer surface of said catheter;
    first conduit means communicating with said balloon for supplying an inflation fluid thereto;
    second conduit means communicating with said annular chamber for conducting fluid to and from said annular chamber; and
    a body of a soft, porous material surrounding said catheter and secured at said outer surface in a region between said first and fourth locations for restricting fluid flow in the passage.

2. A device as defined in claim 1 wherein said fluid transfer member comprises a sheet of elastically expandable flexible material provided with perforations, and a supporting element in the form of a self-supporting sheet of perforated material disposed between said sheet of flexible material and said catheter for holding said sheet of flexible material in a position in which said sheet of flexible material extends radially outwardly from said catheter and for allowing bidirectional fluid flow through the perforations in said sheet of flexible material.

3. A device as defined in claim 2 wherein said supporting element comprises a metal wire screen.

4. A device as defined in claim 2 wherein said sheet of flexible material is elastically expandable in a manner to increase the diameters of the perforations therein.

5. A device as defined in claim 1 wherein said first conduit means comprises a balloon inflation passage extending through the interior of said catheter from said proximal end, and said second conduit means comprises a treatment chemical flow passage extending through the interior of said catheter from said proximal end.

6. A device as defined in claim 5 wherein said treatment chemical flow passage, said bypass flow passage and said balloon inflation passage are the only passages in said catheter.

7. A medical or biological treatment device for supplying a treatment chemical to a region of a physiologic passage, said device comprising:
    a catheter having an outer surface, a distal end and a proximal end and having a bypass flow passage extending from the outer surface of said catheter at a first location between said proximal and distal ends and along the interior of said catheter to an outlet opening at a second location spaced distally from said first location to allow unimpeded low pressure blood or fluid flow to organs downstream of said catheter;
    an inflatable balloon extending around said catheter and secured at said outer surface of said catheter at a third location between said first and second locations;
    a perforated fluid transfer member carried by said catheter and secured at said outer surface of said catheter at a fourth location between said first and third locations, said fluid transfer member being configured to define an annular chamber with said outer surface of said catheter;
    first conduit means communicating with said balloon for supplying an inflation fluid thereto; and
    second conduit means communicating with said annular chamber for conducting fluid to and from said annular chamber, wherein said fluid transfer member comprises a perforated sheet of flexible, elastically expandable material, and a supporting element in the form of a self-supporting sheet of perforated material disposed between said sheet of flexible material and said catheter for holding said sheet of flexible material in a position in which it extends radially outwardly from said catheter and for allowing bidirectional fluid flow through the perforations in said sheet of flexible material.

8. A device as defined in claim 7 wherein said supporting element comprises a metal wire screen.

9. A device as defined in claim 7 wherein said sheet of flexible material is elastically expandable in a manner to increase the diameters of the perforations therein.

10. A device as defined in claim 7, wherein said first conduit means comprises a balloon inflation passage extending through the interior of said catheter from said proximal end, and said second conduit means comprises a treatment chemical flow passage extending through the interior of said catheter from said proximal end.

11. A device as defined in claim 10 wherein said treatment chemical flow passage, said blood bypass flow passage and said balloon inflation passage are the only passages in said catheter.

12. A medical or biological treatment device for supplying a treatment chemical to a region of a physiologic passage, said device comprising:
    a catheter having an outer surface, a distal end and a proximal end and having a bypass flow passage extending from the outer surface of said catheter at a first location between said proximal and distal ends and along the interior of said catheter to an outlet opening at a second location spaced distally from said first location to allow unimpeded low pressure blood or fluid flow to organs downstream of said catheter;
    an inflatable balloon extending around said catheter and secured at said outer surface of said catheter at a third location between said first and second locations;

a perforated fluid transfer member carried by said catheter and secured at said outer surface of said catheter at a fourth location between said first and third locations, said fluid transfer member being configured to define an annular chamber with said outer surface of said catheter;

first conduit means communicating with said balloon for supplying an inflation fluid thereto; and second conduit means communicating with said annular chamber for conducting fluid to and from said annular chamber, wherein: said fluid transfer member is a substantially rigid cylindrical body provided with perforations and defining, with said outer surface of said catheter, for restricting fluid flow in the passage an annular chamber; said first conduit means comprise a first tube located outside of said catheter and extending from said proximal end; and said second conduit means comprise a second tube located outside of said catheter and extending from said proximal end for supplying a treatment chemical to said annular chamber, and a third tube located outside of said catheter and extending from said proximal end for conducting fluid samples from said annular chamber.

13. A device as defined in claim 12 wherein said bypass flow passage is the only passage in said catheter.

14. A medical or biological treatment device for supplying a treatment chemical to a region of a physiologic passage, said device comprising:

a catheter having an outer surface, a distal end and a proximal end and having a bypass flow passage extending from the outer surface of said catheter at a first location between said proximal and distal ends and along the interior of said catheter to an outlet opening at a second location spaced distally from said first location to allow unimpeded low pressure blood or fluid flow to organs downstream of said catheter;

an inflatable balloon extending around said catheter and secured at said outer surface of said catheter at a third location between said first and second locations;

a perforated fluid transfer member carried by said catheter and secured at said outer surface of said catheter at a fourth location between said first and third locations, said fluid transfer member being configured to define an annular chamber with said outer surface of said catheter;

first conduit means communicating with said balloon for supplying an inflation fluid thereto;

second conduit means communicating with said annular chamber for conducting fluid to and from said annular chamber, and an element supported by said outer surface of said catheter and containing a chemical or biological material in a form to be released at a selected rate into a fluid surrounding said catheter.

* * * * *